(12) United States Patent
Bunnelle et al.

(10) Patent No.: US 9,555,152 B2
(45) Date of Patent: Jan. 31, 2017

(54) ARTICLE WITH TACKIFIER-FREE ADHESIVE

(71) Applicant: The Procter & Gamble Company, Cincinnati, OH (US)

(72) Inventors: William L. Bunnelle, Ham Lake, MN (US); Robert Haines Turner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/968,932

(22) Filed: Dec. 15, 2015

(65) Prior Publication Data

US 2016/0095952 A1   Apr. 7, 2016

Related U.S. Application Data

(63) Continuation of application No. 14/302,725, filed on Jun. 12, 2014, now Pat. No. 9,241,843, which is a continuation-in-part of application No. 13/836,385, filed on Mar. 15, 2013, now Pat. No. 8,865,824.

(60) Provisional application No. 61/702,950, filed on Sep. 19, 2012.

(51) Int. Cl.
| | |
|---|---|
| *C08L 53/00* | (2006.01) |
| *A61L 15/58* | (2006.01) |
| *A61F 13/49* | (2006.01) |
| *A61F 13/15* | (2006.01) |
| *B32B 7/12* | (2006.01) |
| *C09J 123/14* | (2006.01) |
| *C09J 123/18* | (2006.01) |
| *C09J 123/20* | (2006.01) |
| *C08L 23/10* | (2006.01) |
| *C08L 23/12* | (2006.01) |
| *C08L 23/14* | (2006.01) |
| *C08L 23/16* | (2006.01) |
| *C08L 23/18* | (2006.01) |
| *A61F 13/515* | (2006.01) |

(52) U.S. Cl.
CPC ........ *A61L 15/585* (2013.01); *A61F 13/15699* (2013.01); *A61F 13/4906* (2013.01); *A61F 13/49019* (2013.01); *A61F 13/515* (2013.01); *B32B 7/12* (2013.01); *C08L 23/10* (2013.01); *C08L 23/12* (2013.01); *C08L 23/14* (2013.01); *C08L 23/16* (2013.01); *C08L 23/18* (2013.01); *C09J 123/14* (2013.01); *C09J 123/142* (2013.01); *C09J 123/18* (2013.01); *C09J 123/20* (2013.01); *C08L 2205/02* (2013.01); *C08L 2205/03* (2013.01); *C08L 2207/02* (2013.01)

(58) Field of Classification Search
CPC . A61L 15/585; A61F 13/515; A61F 13/49019

USPC .......................................................... 524/505
See application file for complete search history.

(56) References Cited

U.S. PATENT DOCUMENTS

| | | |
|---|---|---|
| 3,338,992 A | 8/1967 | Allison |
| 3,341,394 A | 9/1967 | Allison |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,848,594 A | 11/1974 | Buell |
| 3,849,241 A | 11/1974 | Butin et al. |
| 3,860,003 A | 1/1975 | Buell |
| 4,046,945 A | 9/1977 | Baxmann et al. |
| 4,340,563 A | 7/1982 | Appel et al. |
| 4,610,678 A | 9/1986 | Weisman et al. |
| 4,662,875 A | 5/1987 | Hirotsu et al. |
| 4,673,402 A | 6/1987 | Weisman et al. |
| 4,699,622 A | 10/1987 | Toussant et al. |
| 4,761,450 A | 8/1988 | Lakshmanan et al. |
| 4,808,178 A | 2/1989 | Aziz et al. |
| 4,834,735 A | 5/1989 | Alemany et al. |
| 4,846,815 A | 7/1989 | Scripps |
| 4,857,594 A | 8/1989 | Lakshmanan et al. |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,940,464 A | 7/1990 | VanGompel et al. |
| 4,946,527 A | 8/1990 | Battrell |
| 4,963,140 A | 10/1990 | Robertson et al. |
| 4,990,147 A | 2/1991 | Freeland |
| 5,037,416 A | 8/1991 | Allen et al. |
| 5,092,861 A | 3/1992 | Nomura et al. |
| 5,137,537 A | 8/1992 | Herron et al. |
| 5,147,345 A | 9/1992 | Young et al. |

(Continued)

FOREIGN PATENT DOCUMENTS

| | | |
|---|---|---|
| WO | WO 95/16746 | 6/1995 |
| WO | WO 02/053669 | 7/2002 |
| WO | WO2013/019507 | 2/2013 |

OTHER PUBLICATIONS

International Search Report and Written Opinion, for PCT/US2013/060660, mailed Jan. 7, 2014 (10 pages).

(Continued)

*Primary Examiner* — Hui Chin

(74) *Attorney, Agent, or Firm* — Kathleen Y. Carter

(57) ABSTRACT

Disposable absorbent articles assembled from a collection of components using an adhesive comprising an amorphous polyolefin composition and a heterophase polyolefin composition comprising amorphous character and crystalline blocks.

17 Claims, 1 Drawing Sheet

(56) References Cited

U.S. PATENT DOCUMENTS

| | | |
|---|---|---|
| 5,151,092 A | 9/1992 | Buell et al. |
| 5,213,881 A | 5/1993 | Timmons et al. |
| 5,217,812 A | 6/1993 | Lee |
| 5,221,274 A | 6/1993 | Buell et al. |
| 5,242,436 A | 9/1993 | Weil et al. |
| 5,246,433 A | 9/1993 | Hasse et al. |
| 5,260,345 A | 11/1993 | Desmarais et al. |
| 5,269,775 A | 12/1993 | Freeland et al. |
| 5,302,675 A | 4/1994 | Sustic et al. |
| 5,342,338 A | 8/1994 | Roe |
| 5,387,207 A | 2/1995 | Dyer et al. |
| 5,391,434 A | 2/1995 | Krutzel |
| 5,397,316 A | 3/1995 | Lavon et al. |
| 5,499,978 A | 3/1996 | Buell et al. |
| 5,507,736 A | 4/1996 | Clear et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,152 A | 1/1997 | Buell et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,637,665 A | 6/1997 | Sustic et al. |
| 5,643,588 A | 7/1997 | Roe et al. |
| 5,681,913 A | 10/1997 | Sustic et al. |
| 5,685,758 A | 11/1997 | Paul et al. |
| 5,714,554 A | 2/1998 | Sustic et al. |
| 5,723,546 A | 3/1998 | Sustic |
| 5,804,519 A | 9/1998 | Riswick et al. |
| 5,865,823 A | 2/1999 | Curro |
| 5,897,545 A | 4/1999 | Kline et al. |
| 5,957,908 A | 9/1999 | Kline et al. |
| 5,998,547 A | 12/1999 | Hohner |
| 6,004,306 A | 12/1999 | Roe et al. |
| 6,107,537 A | 8/2000 | Elder et al. |
| 6,120,487 A | 9/2000 | Ashton |
| 6,120,489 A | 9/2000 | Johnson et al. |
| 6,143,818 A | 11/2000 | Wang et al. |
| 6,218,457 B1 * | 4/2001 | Fralich .................. C09J 123/20 524/270 |
| 6,281,288 B1 | 8/2001 | Bickert et al. |
| 6,432,098 B1 | 8/2002 | Kline et al. |
| 6,486,246 B1 | 11/2002 | Vion |
| 6,489,400 B2 | 12/2002 | Khandpur et al. |
| 6,582,762 B2 | 6/2003 | Faissat et al. |
| 6,657,009 B2 * | 12/2003 | Zhou .................. B32B 5/02 525/191 |
| 6,677,396 B2 | 1/2004 | Tsui et al. |
| 6,747,114 B2 | 6/2004 | Karandinos et al. |
| 6,767,424 B1 | 7/2004 | Butterbach et al. |
| 6,887,941 B2 | 5/2005 | Zhou |
| 6,992,131 B2 | 1/2006 | Faissat et al. |
| 7,067,585 B2 | 6/2006 | Wang et al. |
| 7,163,741 B2 | 1/2007 | Khandpur et al. |
| 7,199,180 B1 | 4/2007 | Simmons et al. |
| 7,262,251 B2 | 8/2007 | Kanderski et al. |
| 7,270,889 B2 | 9/2007 | Campbell et al. |
| 7,348,376 B2 | 3/2008 | Gelles |
| 7,517,579 B2 | 4/2009 | Campbell et al. |
| 7,521,507 B2 | 4/2009 | Lewtas et al. |
| 7,524,910 B2 | 4/2009 | Jiang et al. |
| 7,626,073 B2 | 12/2009 | Catalan |
| 7,927,703 B2 | 4/2011 | Xia et al. |
| 8,017,827 B2 | 9/2011 | Hundorf et al. |
| 8,084,527 B2 | 12/2011 | Paschkowski et al. |
| 8,193,289 B2 | 6/2012 | Abhari et al. |
| 8,226,625 B2 | 7/2012 | Turner et al. |
| 8,226,626 B2 | 7/2012 | Turner et al. |
| 8,231,595 B2 | 7/2012 | Turner et al. |
| 8,388,594 B2 | 3/2013 | Turner et al. |
| 8,496,637 B2 | 7/2013 | Hundorf et al. |
| 8,865,824 B2 | 10/2014 | Bunnelle |
| 2004/0038058 A1 | 2/2004 | Zhou |
| 2004/0204529 A1 | 10/2004 | Gipson |
| 2007/0042193 A1 | 2/2007 | Wang |
| 2007/0055211 A1 | 3/2007 | Shunketsu et al. |
| 2007/0117894 A1 | 5/2007 | Bach et al. |
| 2007/0117907 A1 | 5/2007 | Bach et al. |
| 2007/0142801 A1 | 6/2007 | Zhou et al. |
| 2007/0187032 A1 | 8/2007 | Wang |
| 2008/0312617 A1 | 12/2008 | Hundorf et al. |
| 2008/0312618 A1 | 12/2008 | Hundorf et al. |
| 2008/0319116 A1 | 12/2008 | Fredrickson et al. |
| 2010/0160497 A1 | 6/2010 | Karjala et al. |
| 2011/0021102 A1 | 1/2011 | Inoue et al. |
| 2011/0082256 A1 | 4/2011 | Martinez et al. |
| 2011/0104508 A1 | 5/2011 | Wang et al. |
| 2011/0167074 A1 | 7/2011 | Heinze et al. |
| 2012/0149827 A1 | 6/2012 | Hu et al. |
| 2012/0171466 A1 | 7/2012 | Urbach et al. |
| 2012/0178333 A1 | 7/2012 | Fowler et al. |
| 2012/0328805 A1 | 12/2012 | Davis |
| 2012/0329353 A1 | 12/2012 | Davis et al. |
| 2014/0079919 A1 | 3/2014 | Bunnelle |
| 2014/0296811 A1 | 10/2014 | Bunnelle et al. |

OTHER PUBLICATIONS

Examiner's Report, from AU Application No. 2013203866, mailed Jun. 28, 2013, 6 pages.

ExxonMobil Chemical, "Product datasheets for Vistamaxx", 1 page, Sep. 17, 2012.

INEOS Oligomers, "Indopol Polybutene Product Data", 2 pages, Sep. 17, 2012.

"Linxar 127 Polymer Data Sheet", ExxonMobil Chemical, Nov. 2010 (1 page).

"REXtac LLC, Advance Technology", 1990, 2 pages.

"Vistamaxx 2330 Propylene-based Elastomer", ExxonMobil Chemical, Last updated: Jan. 26, 2011, http://prospector.ides.com/DataView.aspx?E=114449 (2 pages).

International Search Report, PCT/US2014/069985, mailed Mar. 18, 2015, 10 pages.

International Search Report, PCT/US2014/069990, mailed Mar. 19, 2015, 10 pages.

* cited by examiner

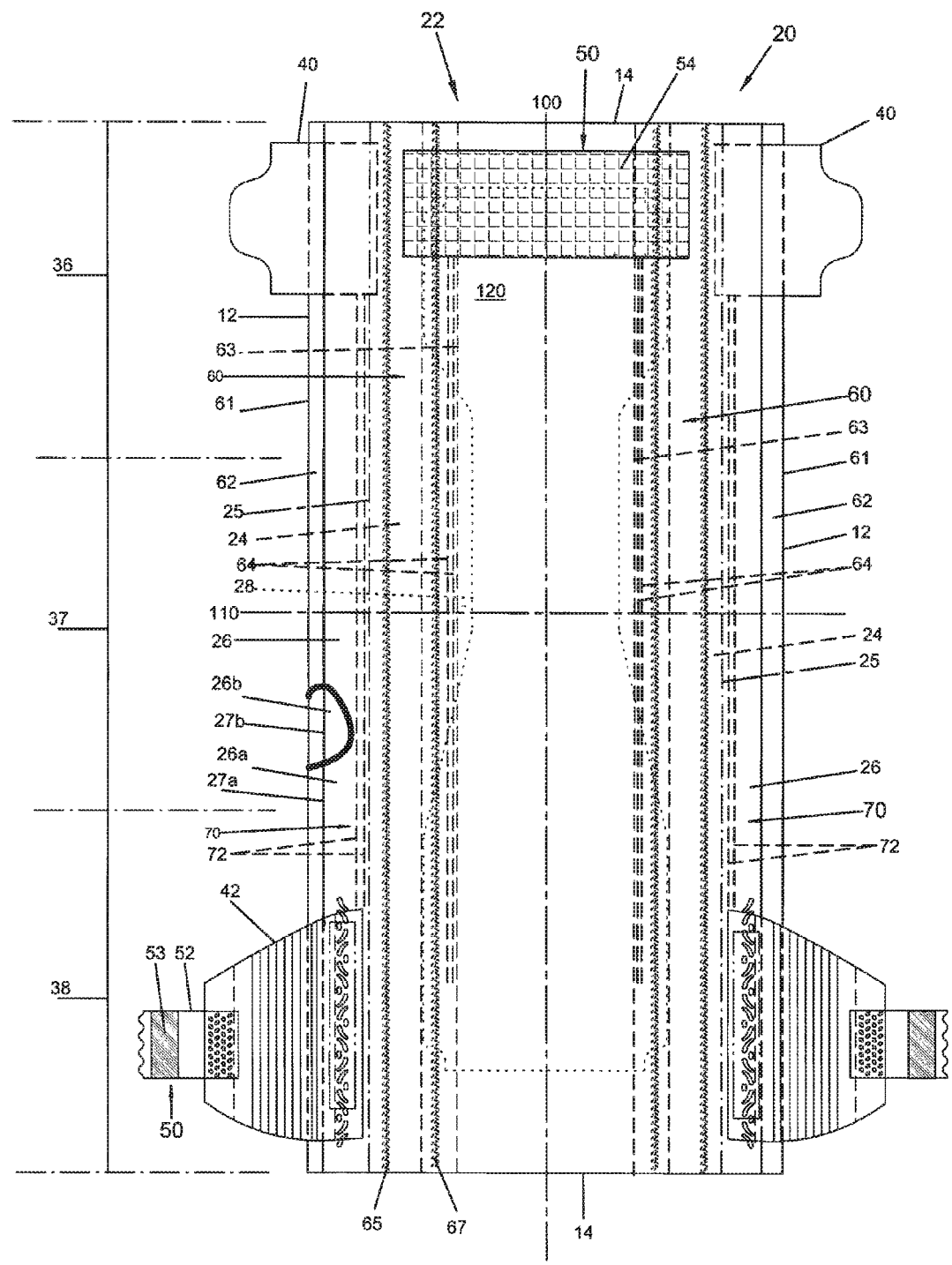

ARTICLE WITH TACKIFIER-FREE ADHESIVE

CROSS-REFERENCE TO RELATED APPLICATIONS

This application is a continuation of U.S. patent application Ser. No. 14/302,725, filed Jun. 12, 2014, which is a continuation-in-part of U.S. patent application Ser. No. 13/836,385, filed Mar. 15, 2013, which claims the benefit of U.S. Provisional Application No. 61/702,950, filed on Sep. 19, 2012, all of which are hereby incorporated by reference.

FIELD

This invention relates to the adhesive material, typically a hot melt adhesive, that is used to assemble components into an absorbent article such as a diaper (i.e. the construction adhesive). In particular, this invention relates to such absorbent articles assembled using a construction adhesive that is substantially free of a tackifier.

BACKGROUND

Users, for example caregivers, rely on disposable absorbent articles to make their lives easier. Disposable absorbent articles, such as adult incontinence articles, diapers, and training pants are generally manufactured by combining several components. These components typically include a liquid-permeable topsheet, a liquid-impermeable backsheet attached to the topsheet, and an absorbent core located between the topsheet and the backsheet. When the disposable article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core generally is designed to have desirable physical properties, e.g. a high absorbent capacity and high absorption rate, so that bodily fluids can be transported from the skin of the wearer into the disposable absorbent article.

Frequently one or more components of a disposable absorbent article are adhesively bonded together. For example, adhesives have been used to bond individual layers of the absorbent article, such as the topsheet and backsheet together. Adhesives have also been used to bond discrete components, such as fasteners and leg elastics or cuffs, to the article. The adhesive is often called a construction adhesive because it is used to help construct the absorbent article from individual components.

In many instances, a hot-melt adhesive is used as a construction adhesive. Common hot-melt adhesives are made by combining polymer and additive components in a substantially uniform thermoplastic blend. Typical additives may include tackifiers, plasticizers, and/or waxes, for example. While such formulations generally work, they can be costly and their performance properties can be improved. For example, tackifiers, which can comprise up to 65% of an adhesive formula, can be expensive and difficult to source. Therefore, there is a continuing need for improved construction adhesives that offer better performance and lower cost.

SUMMARY

The present invention relates to disposable absorbent articles assembled from a collection of components using an adhesive comprising an amorphous polyolefin composition and a heterophase polyolefin composition comprising amorphous character and crystalline blocks.

BRIEF DESCRIPTION OF THE DRAWINGS

FIG. 1 is a plan view of an exemplary absorbent article in a flat, uncontracted state.

DETAILED DESCRIPTION

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, adult incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal".

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Nonwoven" fabric or web means a web having a structure of individual fibers or threads that are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note: to convert from osy to gsm, multiply osy by 33.91.)

"Substrate" is used herein to describe a material that is primarily two-dimensional (i.e., in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers of fibrous materials, nonwovens, and films and foils, such as polymeric films or metallic foils, for example. These materials may be used alone or may comprise two or more layers laminated together. As such, a web may be a substrate or may be a laminate of two or more substrates.

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. Nos. 4,340,563, 3,692,618, 3,802,817, 3,338,992, 3,341,394, 3,502,763, 3,502,538, and 3,542,615. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

"Meltblown fibers" means fibers formed by extruding a molten material, typically thermoplastic in nature, through a plurality of fine, usually circular, die capillaries as molten threads or filaments into converging high-velocity heated gas (e.g., air) streams that attenuate the filaments of molten material to reduce their diameter, which may be to microfiber diameter. Thereafter, the meltblown fibers are carried by the high-velocity gas stream and are deposited on a collecting surface to form a web of randomly dispersed meltblown fibers. Such a process is disclosed for example, in U.S. Pat. No. 3,849,241. Meltblown fibers are microfibers which may be continuous or discontinuous, are generally smaller than 10 microns in diameter, and are generally self-bonding when deposited onto a collecting surface "Microfibers" means small-diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultrafine microfibers. A description of an exemplary process of making ultra-fine microfibers may be found in, for example, U.S. Pat. No. 5,213,881.

"Homopolymer" means a polymer resulting from the polymerization of a single monomer, i.e., a polymer consisting essentially of a single type of repeating unit.

"Copolymer(s)" refers to polymer(s) formed by the polymerization of at least two different monomers. For example, the term "copolymer" includes the copolymerization reaction product of a monomer such as propene or 2-butene, preferably 1-butene and an α-olefin, such as for example, ethylene, 1-hexene or 1-octene.

"Propene copolymer" or "propylene copolymer" means a copolymer of greater than 40 or 50 wt. % or more propene and at least one monomer selected from the group including ethylene and a $C_4$ to $C_{20}$ α-olefin.

"Butene copolymer" means a polymer of n-butene (1-butene) or 2-butene and at least one monomer selected from the group of $C_{2-3}$ and $C_{5-20}$ alpha olefins. Butene copolymers typically comprise a minimum amount at least about 40 or about 50 wt. % or more of a butene monomer such as 1-butene.

"Heterophase" polymer means a polymer having an amorphous character and at least some substantial crystalline content (at least 5 wt. %, 10 wt. %, 20 wt. %, 40 wt. % or 50 wt. % crystalline content) that can provide cohesive strength in the cooled adhesive mass. The crystalline content can be in the form of stereoregular blocks or sequences.

"Amorphous" means the substantial absence of crystallinity, (i.e.) less than 5% and less than 1%.

"Sequence or block" means a polymer portion of repeating monomer that is similar in composition, crystallinity or other aspect.

"Open time" means the amount of time elapsed between application of a molten hot melt adhesive composition to a first substrate, and the time when useful tackiness or wetting out of the adhesive on a substrate effectively ceases due to solidification of the adhesive composition. Open time is also referred to as "working time."

"Substantially" means generally the same or uniform but allowing for or having minor fluctuations from a defined property, definition, etc. For example, small measurable or immeasurable fluctuations in a measured property described herein, such as viscosity, melting point, etc. may result from human error or methodology precision. Other fluctuations are caused by inherent variations in the manufacturing process, thermal history of a formulation, and the like. The adhesive compositions of the, nonetheless, would be said to be substantially having the property as reported.

"Major proportion" means that a material or monomer is used at greater than 50 wt. %.

"Primary component" means that a material or monomer is the more common substance or has the higher concentration in the mixture or polymer compared to others but may not be as much as 50 wt. %.

"Hot-melt processable" means that an adhesive composition may be liquefied using a hot-melt tank (i.e., a system in which the composition is heated so that it is substantially in liquid form) and transported via a pump (e.g., a gear pump or positive-displacement pump) from the tank to the point of application proximate a substrate or other material; or to another tank, system, or unit operation (e.g., a separate system, which may include an additional pump or pumps, for delivering the adhesive to the point of application). Hot-melt tanks used to substantially liquefy a hot-melt adhesive typically operate in a range from about 38° C. to about 230° C. Generally, at the point of application, the substantially liquefied adhesive composition will pass through a nozzle or bank of nozzles, but may pass through some other mechanical element such as a slot. A hot-melt processable adhesive composition is to be contrasted with a composition that requires a conventional extruder, and the attendant pressures and temperatures characteristic of an extruder, to liquefy, mix, and/or convey the composition. While a hot-melt tank and pump in a hot-melt processing system can handle adhesive-composition viscosities in a range from about 1000 centipoise to about 10,000 centipoise, an extruder can handle and process adhesive-composition viscosities in a range from about 10,000 centipoise to viscosities of several hundred thousand centipoise.

Unless otherwise noted, "Laminated structure" or "laminate" means a structure in which one layer, material, component, web, or substrate is adhesively bonded, at least in part, to another layer, material, component, web, or substrate. As stated elsewhere in this application, a layer, material, component, web, or substrate may be folded over and adhesively bonded to itself to form a "laminated structure" or "laminate."

FIG. 1 is a plan view of an exemplary, non-limiting embodiment of a diaper 20 of the present invention in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of chassis 22 is defined by longitudinal side edges 12 and end edges 14. The chassis 22 may have opposing longitudinal side edges 12 that are oriented generally parallel to the longitudinal centerline 100. However, for better fit, longitudinal side edges 12 may be curved or angled to produce, for example, an "hourglass" shape diaper when viewed in a plan view. The chassis 22 may have opposing lend edges 14 that are oriented generally parallel to the lateral centerline 110.

The chassis 22 may comprises a liquid permeable topsheet 24 having longitudinal side edges 25, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. A particularly preferred topsheet 24 is available from BBA Fiberweb, Brentwood, Tenn. as supplier code 055SLPV09U.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. These materials may be combined to provide a core 28 in the form of one or more layers (individual layers not shown) that may include fluid handling layers such as acquisition layers, distribution layers and storage layers. The absorbent core 28 may comprise a substrate layer, absorbent polymer material, and a fibrous layer of adhesive (not shown). Such absorbent cores 28 may also include layers (not shown) to stabilize other core components. Such layers include a core cover and a dusting layer. A suitable material for such layers is a spunbonded/meltblown/spunbonded nonwoven having a basis weight between about 10 and 15 g/m² (the meltblown layer comprises <5 g/m²) as is available from Avgol America, Inc. of Knoxville, N.C. For example, Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; 5,625,222. To reduce the overall size and/or thickness of the absorbent core, and thereby improve wearer comfort and reduce the volume of disposable waste created by a soiled insert, it may be desired to construct an absorbent core using the lowest volumes of core materials possible within performance constraints. Toward this end, examples of suitable materials and constructions for a suitable absorbent core are described in, but are not limited to, U.S. application Ser. Nos. 12/141,122 and 12/141,124; and U.S. Pat. Nos. 8,017,827; and 8,496,637. These generally describe absorbent core constructions that minimize or eliminate the need for and inclusion of airfelt or other forms of cellulose fiber in combination with particles of superabsorbent polymer (hereinafter, "substantially airfelt-free cores"). The adhesives of the present invention may be used within or near the core to immobilize the core, immobilize absorbent material, or to bond the core substrate to the absorbent polymer material, among other uses. The construction of the absorbent core and adhesives used within the core may be such as described in U.S. Pat. Nos. 8,319,005 and 8,187,240, and in U.S. Publication No. 2012/0316530. In some embodiments, the adhesive may be fibrous or be a net-like structure.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer, as illustrated in the cut-away of FIG. 1. The backsheet 26 may comprise an outer cover 26a and an inner layer 26b. The outer cover 26a may have longitudinal side edges 27a and the inner layer 26b may have longitudinal side edges 27b. The outer cover 26a may be made of a soft, non-woven material. The inner layer 26b may be made of a substantially water-impermeable film. The outer cover 26a and an inner layer 26b may be joined together by adhesive or any other suitable material or method. A particularly suitable outer cover 26a is available from Corovin GmbH, Peine, Germany as supplier code A18AH0, and a particularly suitable inner layer 26b is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The diaper 20 may also include a fastening system 50. When fastened, the fastening system 50 interconnects the front waist region 36 and the rear waist region 38 resulting in a waist circumference that may encircle the wearer during wear of the diaper 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

FIG. 1 depicts a fastening system 50 having an engaging member 52 and a receiving member 54. The engaging member 52 is shown having an engaging surface 53 that may comprise hooks, loops, an adhesive, a cohesive, or other fastening member. The receiving member 54 may have a surface that allows for engagement of the engaging member 52. The receiving member 54 may comprise hooks, loops, an adhesive, a cohesive, or other fastening component that can receive the engaging member 52. Suitable engaging member 52 and receiving member 54 combinations include but are not limited to hooks/loop, hooks/hooks, adhesive/polymeric film; cohesive/cohesive, adhesive/adhesive; tab/slot; and button/button hole.

The diaper 20 may include barrier cuffs 60 and/or gasketing cuffs 70. Gasketing cuffs 70 may also be referred to as outer leg cuffs, leg bands, side flaps, leg cuffs, or elastic cuffs. Barrier cuffs 60 may also be referred to as second cuffs, inner leg cuffs or "stand-up" elasticized flaps.

The gasketing cuff 70 may be substantially inelastic or may be elastically extensible to dynamically fit at the wearer's leg. The gasketing cuff 70 may be formed by one or more elastic members 72 (such as elastic strands) operatively joined to the topsheet 24, backsheet 26, or any other suitable substrate used in the formation of the diaper 20. Suitable gasketing cuff construction is further described in U.S. Pat. No. 3,860,003

The barrier cuff 60 may have a distal edge 61 and a proximal edge 63 that run substantially parallel to the longitudinal centerline 100. The barrier cuff 60 may span the entire longitudinal length of the diaper 20. The barrier cuff 60 may be formed by a flap 62 and an elastic member 64 (such as elastic strands). The flap 62 may be a continuous extension of any of the existing materials or elements that form the diaper 20. In other embodiments, such as shown in FIG. 1, the barrier cuff 60 may be a discrete element. In such embodiments, the barrier cuff 60 comprising the flap 62 and the elastic member 64 may be formed then joined to the chassis 22 by a bond 65.

The flap 62 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap 62 may comprise a nonwoven web such as spunbond webs, meltblown webs, carded webs, and combinations thereof (e.g., spunbond-meltblown composites and variants). Laminates of the aforementioned substrates may also be used to form the flap 62. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having barrier cuffs and suitable construction of such barrier cuffs may be found in U.S. Pat. Nos. 4,808,178 and 4,909,803. The elastic member 64 generally spans the longitudinal length of the barrier cuff 60. In other embodiments, the elastic member 64 may span at least the longitudinal length of the barrier cuff 60 within the crotch region 37. It is desirable that the elastic member 64 exhibits sufficient elasticity such that the proximal edge 63 of the barrier cuff 60 remains in contact with the wearer during normal wear, thereby enhancing the barrier properties of the barrier cuff 60. The elastic member 64 may be connected to the flap 62 at opposing longitudinal ends. In certain embodiments, the flap 62 may be folded over onto itself so as to encircle the elastic member 64. A bond 67 may be used to secure the folded section of the flap 62.

The barrier cuffs 60 and/or gasketing cuffs 70 may be treated, in full or in part, with a lotion, as described above with regard to topsheets, or may be fully or partially coated with a hydrophobic surface coating as detailed in U.S. application Ser. No. 11/055,743, which was filed Feb. 10, 2005.

The diaper 20 may include front ears 40 and back ears 42. The front and/or back ears 40, 42 may be unitary elements of the diaper 20 (i.e., they are not separately manipulative elements secured to the diaper 20, but rather are formed from and are extensions of one or more of the various layers of the diaper). In certain embodiments, the front and/or back ears 40, 42 may be discrete elements that are joined to the chassis 22, as shown in FIG. 1. Discrete front and/or back ears 40, 42 may be joined to the chassis 22 by any bonding method known in the art such as adhesive bonding, pressure bonding, heat bonding, and the like. In other embodiments, the front and/or back ears 40, 42 may comprise a discrete element joined to the chassis 22 with the chassis 22 having a layer, element, or substrate that extends over the front and/or back ear 40, 42. The front ears 40 and back ears 42 may be extensible, inextensible, elastic, or inelastic. The front ears 40 and back ears 42 may be formed from nonwoven webs, woven webs, knitted fabrics, polymeric and elastomeric films, apertured films, sponges, foams, scrims, and combinations and laminates thereof. In certain embodiments the front ears 40 and back ears 42 may be formed of a nonwoven/elastomeric material laminate or a nonwoven/elastomeric material/nonwoven laminate. A suitable elastic back ear 42 may be a laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332). While the following embodiments are directed to back ear 42 design and construction, these embodiments are equally applicable to front ear 40 design and construction. It should be recognized that any combination of the following embodiments may be used for the back ear 42 and/or the front ear 40.

In alternative embodiments, the diaper 20 may be preformed by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.). For example, the diaper 20 of FIG. 1 may be manufactured with the fastening system 50 engaged (i.e., the engaging member 52 is joined to the receiving member 54). As an additional example, the diaper 20 of FIG. 1 may be manufactured with the front ears 40 joined to the back ears 42 by way of a bond such as an adhesive bond, a mechanical bond, or some other bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

As noted above, a construction adhesive is typically used to join components of an absorbent article as the absorbent article is being assembled. Nonlimiting examples of such joinder using the construction adhesive include but are not limited to:

core cover to dusting layer sealing;
backsheet 26 to core 28;
elastic member 64 to nonwoven and/or film to form a barrier cuff 60 or a gasketing cuff 70.
nonwoven to vapor permeable film to form a backsheet 26;
barrier cuffs to topsheet 24;
receiving member 54 to topsheet 24;
ear 40, 42 to backsheet 26.
core substrate layer to core absorbent polymer material As will be recognized, many of these uses involve joinder of a nonwoven material to another material. In some instances nonwoven material is joined to another nonwoven. In other instances, a nonwoven may be joined to a film.

Nonwovens in the present invention may be such as those disclosed in U.S. Patent Application No. 61/837,286, U.S. Pat. No. 8,388,594, U.S. Pat. No. 8,226,625, U.S. Pat. No. 8,231,595, and U.S. Pat. No. 8,226,626.

Adhesive

The adhesive material comprises a first polymer comprising a polyolefin comprising a substantially amorphous or randomly polymerized polymer material and a second polymer comprising a heterophase polymer.

The first amorphous polymer comprises typically butene (e.g.) 1-butene and can contain ethylene, propene or a second $C_{4-40}$ olefin polymer. These substantially amorphous low crystallinity polymers have less than 10% and preferably less than 5% crystalline character.

The second heterophase olefin polymer comprises a first poly alpha olefin polymer comprising a substantial proportion (greater than 40 or 50 mole %) of a propene monomer and comprises an amorphous polymer with some crystalline content.

The amorphous polymer is a butene-based copolymer (the minimum amount is at least about 30 or 40 or 50 wt. % of 1-butene), which may also be referred to as a random butene-α-olefin copolymer. The butene copolymer includes one or more units, i.e., mer units, derived from propene, one or more comonomer units derived from ethylene or α-olefins including from 4 to about 20 carbon atoms.

The first copolymer comprises about 30 mole %-about 70 mole %, preferably about 40 mole % to about 60 mole % of units derived from butene. In addition to butene-derived units, the present copolymer contains from about 70 mole %-about 30 mole % to about 60 mole %-about 40 mole %, of units derived from preferably ethylene, propene or at least one $C_5$ to 10 alpha-olefin monomer.

In one or more embodiments, the α-olefin comonomer units can also be derived from other monomers such as ethylene, 1-butene, 1-hexane, 4-methyl-1-pentene and/or 1-octene. Exemplary alpha-olefins are selected from the group consisting of ethylene, butene-1, pentene-1,2-methylpentene-1,3methylbutene-1, hexene-1,3-methylpentene-1, 4-methylpentene-1,3,3-dimethylbutene-1, heptene-1, hexene-1, methylhexene-1, dimethylpentene-1, trimethylbutene-1, ethylpentene-1, octene-1, methylpentene-1, dimethylhexene-1, trimethylpentene-1, ethylhexene-1, methylethylpentene-1, diethylbutene-1, propylpentane-1, decene-1, methylnonene-1, nonene-1, dimethyloctene-1, trimethylheptene-1, ethyloctene-1, methylethylbutene-1, diethylhexene-1, dodecene-1, and hexadodecene-1.

In one or more embodiments, amorphous copolymer comprises about 30 mole %-about 70 mole %, preferably about 40 mole % to about 60 mole % of units derived from butene and from about 70 mole %-about 30 mole % to about 60 mole %-about 40 mole %, of units derived from at least one alpha-olefin monomer selected from ethylene, propene, 1-hexene or 1-octene. Small amounts of α-olefin monomer(s) can be used in the range of about 0.1 to 20 mole %. The amorphous polymer has a weight average molecular weight (Mw) of about 1,000 to about 25,000 or less, preferably about 2,000 to 20,000.

In one or more embodiments, first copolymer comprises about 30 mole %-about 70 mole %, preferably about 40 mole % to about 60 mole % of units derived from butene and from about 70 mole %-about 30 mole % to about 60 mole %-about 40 mole %, of units derived from propene, while small amounts of α-olefin monomer(s) can be used in the range of about 0.1 to 20 mole %.

The amorphous polymer has a weight average molecular weight (Mw) of about 1,000 to about 50,000 or less, preferably about 5,000 to 45,000.

The amorphous copolymer has a viscosity of less than 10,000 mPa·s (1 centipoise [cps]=1 mPa·s), for example about 2000 to 8000 mPa·s, when measured by ASTM D3236 at 190° C. Melt Viscosity was determined according to ASTM D-3236, which is also referred to herein as "viscosity" and/or "Brookfield viscosity".

Some examples of amorphous polyolefin include the Rextac polymers made by Huntsman including Rextac E-63, E-65, 2815, 2830, etc. See, for example Sustic, U.S. Pat. No. 5,723,546 for a description of the polymers and which is expressly incorporated herein. Other useful amorphous polymers are sold as Vistoplast® and Eastoflex® materials.

The adhesive material comprises a second polyolefin comprising a substantially heterophase copolymer. The heterophase polyolefin may comprise a propene copolymer (i.e.) propene-based polymer with other comonomer(s). The propene-based polymer backbone preferably comprises propene and one or more $C_2$ or $C_{4-20}$ α-olefins. The propene-based heterophase polymer, for example, may comprise propene and ethylene, hexene or optionally other $C_2$ or $C_{4-20}$ α-olefins. The polymer comprises about 99.5 to about 70 wt. %, preferably about 95 to about 75 wt. % of units derived from propene. In addition to propene derived units, the present copolymer contains from about 0.1 to 30 wt. % preferably from about 5 to 25 wt. %, of units derived from preferably at least $C_{2-4}$ or a $C_{5-10}$ alpha-olefin.

In one or more embodiments, the second copolymer comprises a major proportion of propene and about 0.1 to 30 wt. %, or 2 to 25 wt. % ethylene. In one or more embodiments, the second copolymer comprises a major proportion of propene and about 0.1 to 30 wt. %, or 2 to 25 wt. % 1-butene.

In one or more embodiments, the second copolymer comprises a major proportion of propene and about 0.1 to 30 wt. %, or 2 to 25 wt. % 1-hexene. In one or more embodiments, the second copolymer comprises a major proportion of propene and about 0.1 to 30 wt. %, or 2 to 25 wt. % 1-octene.

Other comonomer for use in either the first or second polyolefin comprise ethylene or α-olefins containing 4 to 12 carbon atoms. Exemplary α-olefins may be selected from the group consisting of ethylene; 1-butene; 1-pentene; 2-methyl-1-pentene; 3-methyl-1-butene; 1-hexene-3-methyl-1-pentene-4-methyl-1-pentene-3,3-dimethyl-1-butene; 1-heptene; 1-hexene; 1-methyl-1-hexene; dimethyl-1-pentene; trimethyl-1-butene; ethyl-1-pentene; 1-octene; methyl-1-pentene; dimethyl-1-hexene; trimethyl-1-pentene; ethyl-1-hexene; 1-methylethyl-1-pentene; 1-diethyl-1-butene; propyl-1-pentene; 1-decene; methyl-1-nonene; 1-nonene; dimethyl-1-octene; trimethyl-1-heptene; ethyl-1-octene; methylethyl-1-butene; diethyl-1-hexene; 1-dodecene and 1-hexadodecene. Preferred $C_{4-10}$ alpha-olefins are those having 6 to 8 carbon atoms, with the most preferred alpha-olefin being 1-hexene and 1-octene.

Preferred propene copolymers are copolymers wherein the comonomer is ethylene, 1-butene, 1-hexene or 1-octene. The stereo-regular (isotactic or syndiotactic) sequence or block content of the polymers imparts a heterophase (partial amorphous and partial crystalline) character of crystallizable content to the polymers. As used herein and as applied to semi-crystalline heterophase copolymers, the term "crystallizable" describes those polymer sequences or blocks that can crystallize upon cooling. Crystalline content of the solidified semicrystalline copolymers increases the cohesive strength of the hot melt adhesives. Hot melt adhesive formulations based on metallocene polymerized semicrystalline copolymers can eventually build sufficient crystalline content over time to achieve good cohesive strength in the formulation.

The second heterophase polymer comprises crystallizable polymer blocks or sequences, preferably of stereoregular sequences of polymerized monomer such as ethylene or propene, which sequences are long enough to crystallize, typically at least repeating or block monomer units per sequence.

In preferred embodiments, the crystallizable segments can be stereoregular or isotactic. Isotacticity of the olefin sequences can be achieved by polymerization with the choice of a desirable catalyst composition. The isotacticity is conventionally measured using DSC or C-13 NMR instrumental techniques.

The heterophase polymer has a crystallinity of at least 5 wt. %, 10 wt. %, 20 wt. %, 40 wt. % or 50 wt. %, preferably between 20% and 80%, more preferably between 25% and 70%.

The heat of fusion of the heterophase copolymers (by ASTM E793) is about 10 J/g to about 70 J/g and about 15

J/g to about 70 J/g, with a melting point less than 150° C. and about 105° C. to about 135° C.

The heterophase polymer has a weight average molecular weight (Mw) of about 20,000 or less, preferably about 10,000 or less, preferably about 500 to 8,000.

The heterophase copolymer has a viscosity of less than 20,000 mPa·s (1 centipoise [cps]=1 mPa·s), for example less than 15000 mPa·s, in certain application less than 10,000 mPa·s and less than 5,000 mPa·s when measured at 190° C. using a Brookfield viscometer (as measured by ASTM D 3236) which is also referred to herein as "viscosity" and/or "Brookfield viscosity."

Some examples of heterophase polymers useful in the hot melt adhesive compositions of include polyolefin such as polyethylene, polypropylene, and copolymers thereof such as polypropylene based elastomers sold by ExxonMobil Chemical of Houston, Tex. under the trade name VISTA-MAXX™ and polyethylene based elastomers such as those sold by Dow Chemical Company of Midland, Mich. under the trade names AFFINITY™ and ENGAGE™.

Other heterophase polymers that are useful in the hot melt adhesive compositions include the polyolefin elastomers VISTAMAXX™ 8816, VISTAMAXX™ 2230, and ENGAGE™ 8200. AFFINITY™ GA 1900 has a density of 0.870 g/cm3 according to ASTM D792, heat of fusion of 46.1 J/g, and a Brookfield viscosity of 8200 cP at 177° C. according to ASTM D 1084. AFFINITY™ GA 1950 has a density of 0.874 g/cm3 according to ASTM D792, heat of fusion of 53.4 J/g, and a Brookfield viscosity of 17,000 cP at 177° C. according to ASTM D 1084. ENGAGE™ 8200 has a density of 0.87 g/cm3 according to ASTM D792 and a melt index of 5 g/10 min at 190° C. These olefin elastomers are compatible with the propylene copolymers useful in the hot melt adhesive compositions and improve physical properties such as low temperature adhesive performance without sacrificing effective set time.

Any conventional polymerization synthesis processes may prepare the polyolefin copolymers. Preferably, one or more catalysts, which are typically metallocene catalysts or Zeigler-Natta, catalysts, are used for polymerization of an olefin monomer or monomer mixture. Polymerization methods include high pressure, slurry, gas, bulk, suspension, supercritical, or solution phase, or a combination thereof, preferably using a single-site metallocene catalyst system. The catalysts can be in the form of a homogeneous solution, supported, or a combination thereof. Polymerization may be carried out by a continuous, a semi-continuous or batch process and may include use of chain transfer agents, scavengers, or other such additives as deemed applicable. By continuous is meant a system that operates (or is intended to operate) without interruption or cessation. For example a continuous process to produce a polymer would be one where the reactants are continually introduced into one or more reactors and polymer product is continually withdrawn. In one embodiment, the propene copolymer described herein is produced in a single or multiple polymerization zones using a single polymerization catalyst. The heterophase polymers are typically made using multiple metallocene catalyst blends that obtain desired heterophase structure.

The compositions disclosed herein can also comprise a plasticizer or plasticizing oil or extender oil that may reduce viscosity or improve tack properties in the adhesive. Any plasticizer known to a person of ordinary skill in the art may be used in the adhesion composition disclosed herein. Non-limiting examples of plasticizers include olefin oligomers, low molecular weight polyolefin such as liquid polybutene, low molecular weight non-aromatic polymers (e.g. REGAL-REZ 101 from Eastman Chemical Company), phthalates, mineral oils such as naphthenic, paraffinic, or hydrogenated (white) oils (e.g. Kaydol oil or ParaLux oils (Chevron U.S.A. Inc.)), vegetable and animal oil and their derivatives, petroleum derived oils, and combinations thereof. Low molecular weight polyolefin may include those with Mw as low as 100, in particular, those in the range of from about 100 to 3000, in the range of from about 250 to about 2000 and in the range of from about 300 to about 1000.

In some embodiments, the plasticizers include polypropylene, polybutene, hydrogenated polyisoprene, hydrogenated polybutadiene, polypiperylene, copolymers of piperylene and isoprene, and the like, having average molecular weights between about 350 and about 10,000. In other embodiments, the plasticizers include glyceryl esters of the usual fatty acids and polymerization products thereof. In some embodiments, the plasticizer may be a polymer of isobutylene. A preferred plasticizer comprises a polyisobutylene polymer. The polymer can comprise major proportion of isobutylene units or can be represented as:

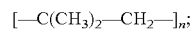

wherein n=15 to 75. Polyisobutylene materials are viscous liquids with molecular weight of about 200-20,000, about 200-5,000 or about 500-2,000. The preferred materials have a Saybolt Universal seconds (SUS) viscosity at 100° C. of about 100 to 20,000. The characteristic features of polyisobutylene are low gas permeability and high resistance to the action of acids, alkalis, and solutions of salts, as well as high dielectric indexes. They degrade gradually under the action of sunlight and ultraviolet rays (the addition of carbon black slows this process). In industry, polyisobutylene is produced by ionic (AlCl$_3$ catalyzed) polymerization of the monomer at temperatures from −80° to −100° C.; they are processed using the ordinary equipment of the rubber industry. Polyisobutylene combines easily with natural or synthetic rubbers, polyethylene, polyvinyl chloride, and phenol-formaldehyde resins.

Embodiments of preferred compositions are made with substantially less than 40 wt. %, less than 20 wt. % or are substantially free of an effective amount of a conventional tackifier material that can add any aspect of open time, substrate wetting or tack to the adhesive material. Avoiding the use of a tackifier reduces adhesive density, adhesive and product costs and frees formulators from the use of materials in short supply. Further, tackifier can impart undesirable odor in disposable articles and can also act as carriers of low molecular weight plasticizers (like process oils that are used in SBC based adhesives) that can weaken the polyethylene backsheet materials used in articles. Backsheet integrity is becoming more important due to the downsizing of the polyethylene film thickness used in these articles. The term "conventional tackifier resins", means those resins commonly available in the adhesive art and industry that are used in typical hot melt adhesives. Examples of conventional tackifing resins included in this range include an aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, poly-terpene, aromatic modified poly-terpene, terpene-phenolic, aromatic modified hydrogenated poly-cyclopentadiene resins, hydrogenated aliphatic resins, hydrogenated aliphatic aromatic resins, hydrogenated terpene and modified terpene and hydrogenated rosin esters. Often in conventional formulations such resins are used in amounts that range from about 40 to about 65 wt. %.

In further embodiments, the compositions disclosed herein optionally can comprise an antioxidant or a stabilizer. Any antioxidant known to a person of ordinary skill in the art may be used in the adhesion composition disclosed herein. Non-limiting examples of suitable antioxidants include amine-based antioxidants such as alkyl diphenyl amines, phenyl-naphthylamine, alkyl or aralkyl substituted phenylnaphthylamine, alkylated p-phenylene diamines, tetramethyl-diaminodiphenylamine and the like; and hindered phenol compounds such as 2,6-di-t-butyl-4-methyl-phenol; 1,3,5-trimethyl-2,4,6-tris(3',5'-di-t-butyl-4'-hydroxybenzyl)benzene; tetrakis [(methylene(3,5-di-t-butyl-4-hydroxyhydrocinnamate)]methane (e.g., IRGANOX™1010, from Ciba Geigy, N.Y.); octadecyl-3,5-di-t-butyl-4-hydroxycinnamate (e.g., IRGANOX™1076, commercially available from Ciba Geigy) and combinations thereof. Where used, the amount of the antioxidant in the composition can be from about greater than 0 to about 1 wt. %, from about 0.05 to about 0.75 wt. %, or from about 0.1 to about 0.5 wt. % of the total weight of the composition.

In further embodiments, the compositions disclosed herein optionally can comprise an UV stabilizer that may prevent or reduce the degradation of the composition by radiation. Any UV stabilizer known to a person of ordinary skill in the art may be used in the adhesion composition disclosed herein. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds and combinations thereof. Where used, the amount of the UV stabilizer in the composition can be from about greater than 0 to about 1 wt. %, from about 0.05 to about 0.75 wt. %, or from about 0.1 to about 0.5 wt. % of the total weight of the composition.

In further embodiments, the compositions disclosed herein optionally can comprise a brightener, colorant or pigment. Any colorant or pigment known to a person of ordinary skill in the art may be used in the adhesion composition disclosed herein. Non-limiting examples of suitable brighteners, colorants or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant or pigment in the composition can be from about greater than 0 to about 10 wt %, from about 0.01 to about 5 wt %, or from about 0.1 to about 2 wt % of the total weight of the composition.

The compositions disclosed herein may also optionally comprise a fragrance such as a perfume or other odorant. Such fragrances may be retained by a liner or contained in release agents such as microcapsules that may, for example, release fragrance upon removal of a release liner from or compression on the composition.

In further embodiments, the compositions disclosed herein optionally can comprise filler. Any filler known to a person of ordinary skill in the art may be used in the adhesion composition disclosed herein. Non-limiting examples of suitable fillers include sand, talc, dolomite, calcium carbonate, clay, silica, mica, wollastonite, feldspar, aluminum silicate, alumina, hydrated alumina, glass bead, glass microsphere, ceramic microsphere, thermoplastic microsphere, barite, wood flour, and combinations thereof. Where used, the amount of the filler in the composition can be from about greater than 0 to about 60 wt. %, from about 1 to about 50 wt. %, or from about 5 to about 40 wt. %.

TABLE 1

Substantially Tackifier-Free Adhesive Compositions

| Component | Embodiment | Wt. % | Wt. % | Wt % |
|---|---|---|---|---|
| Amorphous polymer | REXTAC E65 | 90-10 | 20-80 | 70-40 |
| Heterophase polymer | Vistamaxx | 10-90 | 80-20 | 40-70 |
| Plasticizer | Polyisobutylene | 0-40 | 5-35 | 5-30 |
| Additive | Antioxidant/Stabilizer | 0-20 | 1-20 | 1-15 |

One substantial advantage in the claimed adhesives relates to a density of the adhesive formulations. Conventional tackifier is at a density that often ranges from about 1.07-1.09 g-cm$^{-3}$. Conventional formulated adhesives containing a conventional tackifier in amounts of about 40 to 60 wt. %, have a density greater than 0.9 g-cm$^{-3}$ or more. The formulated adhesives of the invention, substantially free of tackifier, have densities less than 0.9 g-cm$^{-3}$, often in the range about 0.85-0.89 g-cm$^{-3}$, often 0.86-0.87 g-cm$^{-3}$. Not only are these adhesives free of the problems arising from tackifier materials, but the use of the claimed adhesives, and a lower density, permits the use of a reduced amount when measured by weight, resulting in cost savings.

Another aspect are methods of manufacture employing the hot melt adhesive compositions. The method involves application of the molten compositions to a substrate, followed by contact of the adhesive composition with a second substrate within 0.1 second to 5 seconds after application of the adhesive composition to the first substrate, wherein the contacting results in an adhesive bond between the substrates.

The hot melt adhesive compositions have melt rheology and thermal stability suitable for use with conventional hot melt adhesive application equipment. The blended components of the hot melt adhesive compositions have low melt viscosity at the application temperature, thereby facilitating flow of the compositions through a coating apparatus, e.g., coating die or nozzle, without resorting to the inclusion of solvents or extender oil into the composition. Melt viscosities of the hot melt adhesive compositions are between 1500 cP and 3500 cP or about 2000 cP to 3000 cP in mille Pascal-seconds or centipoise (cP) using a Brookfield thermosel RVT viscometer using a rotor number 27 at 176.66° C. (50 rpm, 350° F.). The hot melt adhesive compositions have a softening point (ASTM D 3461-97 Standard Test Method for Mettler Softening Point Method) of about 80° C. to 140° C., in some embodiments about 115° C. to 130° C. For certain applications, the hot melt adhesive compositions have effective set times of about 5 seconds or less, for example about 0.1 second to 5 seconds, in some embodiments about 0.1 second to 3 seconds, and in some embodiments about 0.2 second to 1 second. The effective set time of the hot melt adhesives are unexpectedly short, particularly given that the open time remains in the acceptable range.

The construction adhesive can be applied using a wide variety of known application methods including but not limited to slot extrusion, sprays, including spiral sprays, and beads. Specific examples include but are not limited to:

application of the construction adhesive in a spiral spray or slot coating to join a topsheet to an underlying nonwoven layer;

application of the construction adhesive via slot coating to join an acquisition layer or a distribution layer to a core cover;

application of beads of the construction adhesive located between the nonwoven material comprising the cuff and the backsheet;

application of the construction adhesive in a spiral spray or slot coating to join the topsheet to the backsheet so as to seal the longitudinal edges of the absorbent article;

application of the construction adhesive using slot coating to join a landing zone (i. e. a receiving member) to the backsheet;

application of the construction adhesive using slot coating to join the core cover to the dusting layer;

application of the construction adhesive in a spiral spray to join the core to the backsheet.

application of the construction adhesive in a spiral spray to join the nonwoven material comprising the cuff to the nonwoven material comprising the backsheet.

EXAMPLES

A number of hot melt adhesive compositions were prepared by blending first amorphous copolymer, second heterophase copolymer, polymer plasticizer/diluent and antioxidant under mixing conditions at elevated temperatures to form a fully homogenized fluid melt. Mixing temperatures varied from about 135 to about 200° C., preferably about 150 to about 175° C. A WiseStir® mixer was used to ensure full homogenization of components into a final adhesive composition.

Examples 1-4

Hot melt adhesive compositions were formulated by melt blending as described below, wherein specific components and amounts of the components are shown in the following table 2.

TABLE 2

Exemplary Adhesive Formulations

| Source | Component | Ex. 1 wt. % | Ex. 2 wt. % | Ex. 3 wt. % | Ex. 4 wt. % | Ex. 5 wt. % | Ex. 6 wt. % | Ex. 7 wt. % | Ex. 8 wt. % |
|---|---|---|---|---|---|---|---|---|---|
| ExxonMobil Chemical, Houston, TX | Vistamaxx 8816 | 20 | 35 | 35 | 35 | 15 | 15 | 15 | 10 |
| Huntsman Chemicals | Rextac E-65 | 59.5 | 60 | 55 | 50 | 64.5 | 59.5 | 59.5 | 59.5 |
| Ineos Chemicals | Indapol H-300 (Polyisobutylene) | 20 | 4.5 | 9.5 | 14.5 | 20 | 24.99 | 0 | 0 |
| Ineos Chemicals | Indapol H-1900 (Polyisobutylene) | 0 | 0 | 0 | 0 | 0 | 0.5 | 0.5 | 0.5 |
| Ciba Geigy Ltd., Basel, Switzerland | Irganox 1010 (Hindered Phenol) | 0.5 | 0.5 | 0.5 | 0.5 | 0.5 | 0.5 | 0.5 | 0.5 |
| Mayzo, Inc. Fluorescent Optical Brightener | Benetex OB | 0 | 0 | 0 | 0 | 0 | 0.01 | 0.01 | 0.01 |

TABLE 3

Exemplary Adhesive Viscosity Data

| Brookfield Viscosity @ | Ex. 1 | Ex. 2 | Ex. 3 | Ex. 4 | Ex. 5 | Ex. 6 | Ex. 7 | Ex. 8 |
|---|---|---|---|---|---|---|---|---|
| 121.1° C. (250° F.) | 26200 | | | | 29750 | 16600 | | 39000 |
| 135° C. (275° F.) | 7710 | 12125 | 9725 | 7500 | 8425 | 7100 | 9100 | 8750 |
| 148.9° C. (300° F.) | 4675 | 6350 | 5325 | 4525 | 5150 | 4200 | 5325 | 5375 |
| 162.8° C. (325° F.) | 3075 | 4190 | 3500 | 2980 | 3475 | 2800 | 3550 | 3375 |
| 176.7° C. (350° F.) | 2220 | 2945 | 2450 | 2080 | 2315 | 1920 | 2385 | 2275 |
| Mettler Softening Point (° C.) | 121 | 125 | 125 | 124 | 120 | 118 | 118 | 115 |
| Density g/cm$^3$ ASTM 792 | 0.86-0.87 | 0.86-0.87 | 0.86-0.87 | 0.86-0.87 | 0.86-0.87 | 0.86-0.87 | 0.86-0.87 | 0.86-0.87 |

The adhesive is typically applied in an amount of about 1 to about 100 or about 4 to about 90 or about 7 to about 70 grams per square meter (g/m$^2$) of resulting bonded material. The material may be applied in an amount of about 0.1 to about 20 or about 0.2 to about 10 or about 0.3 to about 15 grams per square meter (g/m$^2$) of resulting bonded material. The adhesive material can be used at an add-on rate of 0.5 to 2 g/m$^2$, 0.6 to 1.7 g/m$^2$ or 0.7 to 1.5 g/m$^2$, for absorbent articles.

These data indicates that the materials will provide excellent construction bonding in disposable absorbent articles. Note viscosity relates to the resistance to flow of the material under certain conditions. This distinctive property determines the flowability, degree of wetting, and penetration of the substrate by the molten polymer. It provides an indication of its processability and utility as a hot melt adhesive material. Melt viscosity is generally directly related to a polymer molecular weight and is reported in Millipascalsecond's or centipoise (cP) using a Brookfield thermosel RVT viscometer using a rotor number 27 at the stated temperature.

Mettler softening point in degrees Centigrade or degrees Fahrenheit is typically measured using ASTM D3104. The amorphous nature of the polyolefin materials results in a melting point that is not sharp or definite. Rather as the temperature increases, amorphous polymers gradually change from a solid to a soft and then to a liquid material. No clearly defined glass transition or melting temperature is often noted. This temperature testament that generally measures the precise temperature at which a disc of polymer sample, heated at a rate of 2° C. per minute or 10° F. per minute becomes soft enough to allow the test object, a steel ball (grams) drops through the sample. The softening point of a polymer reported in degrees Centigrade or degrees Fahrenheit is important because it typically indicates the polymer's heat resistance, useful application temperatures and solidification points.

The claims may suitably comprise, consist of, or consist essentially of, or be substantially free of any of the disclosed or recited elements. The invention illustratively disclosed herein can also be suitably practiced in the absence of any element which is not specifically disclosed herein.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a longitudinal centerline and a lateral centerline, a front waist region with a front waist edge, a rear waist region with a rear waist edge, a crotch region disposed between said front and rear waist regions and two spaced apart longitudinal side edges joining said front waist edge to said rear waist edge and comprising an assembly of components including:
   a) a topsheet;
   b) a backsheet underlying said topsheet;
   c) an absorbent core disposed between said topsheet and said backsheet, wherein said absorbent core comprises at least one of a core cover, a dusting layer, an acquisition layer, a distribution layer and a storage member;
   d) at least one additional component selected from the group consisting of:
      i) a fastening system for joining said front waist region to said rear waist region when said absorbent article is worn;
      ii) barrier cuffs lying adjacent and inboard one of said longitudinal side edges;
      iii) gasketing cuffs lying between said longitudinal side edge and said barrier cuff;
      iv) front ears disposed in said front waist region;
      v) back ears disposed in said rear waist region; and
      vi) a receiving member; and
   e) a hot melt adhesive composition joining at least two absorbent article components together, wherein said adhesive composition comprises:
      (i) about 40-70 wt. % of an amorphous polyolefin composition comprising greater than 40 mole % 1-butene;
      (ii) about 70-40 wt. % of a heterophase polyolefin composition having a molecular weight (Mw) less than 10,000, comprising a propene and a monomer selected from ethylene, 1-hexene, 1-octene or combinations thereof; and
      (iii) about 0.1 to 30 wt. % of a polyisobutylene plasticizer polymerized with $AlCl_3$ and having a molecular weight (Mw) of 200-5000.

2. The absorbent article of claim 1, wherein said hot melt adhesive joins said topsheet to an underlying nonwoven layer.

3. The absorbent article of claim 1, wherein said hot melt adhesive joins an elastic material to a nonwoven material to form said barrier cuffs.

4. The absorbent article of claim 1, wherein said hot melt adhesive joins an elastic material to said backsheet.

5. The absorbent article of claim 1, wherein said hot melt adhesive joins the acquisition layer to the core cover.

6. The absorbent article of claim 1, wherein said hot melt adhesive joins the distribution layer to the core cover.

7. The absorbent article of claim 1, wherein said hot melt adhesive joins the topsheet to the backsheet adjacent a longitudinal edge of said absorbent article.

8. The absorbent article of claim 1, wherein said hot melt adhesive joins the receiving member to the backsheet.

9. The absorbent article of claim 1, wherein said hot melt adhesive joins the core cover to the dusting layer.

10. The absorbent article of claim 1, wherein said hot melt adhesive joins the core cover to the backsheet.

11. The absorbent article of claim 1, wherein said hot melt adhesive joins the dusting layer to the backsheet.

12. The absorbent article of claim 1, wherein the heterophase polyolefin comprises at least about 5 wt. % crystalline sequences or blocks.

13. The absorbent article of claim 1, wherein the heterophase polyolefin comprises greater than 40 wt. % of propene and less than 60 wt. % of the monomer and has a crystallinity of greater than 10%.

14. The absorbent article of claim 1, wherein the adhesive is substantially free of a tackifier.

15. The absorbent article of claim 1, wherein the heterophase polyolefin composition comprises greater than 40 wt. % of propene and less than 60 wt. % of the monomer selected from ethylene, 1-hexene, 1-octene or combinations thereof and has a crystallinity of greater than 10%.

16. The absorbent article of claim 1, wherein the adhesive composition comprises about 40 wt. % to about 50 wt. % of the heterophase polyolefin composition.

17. The absorbent article of claim 1, wherein the plasticizer comprises a
polyisobutylene with a molecular weight of about 500 to about 2000.

* * * * *